US011583200B2

(12) United States Patent
Han et al.

(10) Patent No.: US 11,583,200 B2
(45) Date of Patent: Feb. 21, 2023

(54) ELECTRONIC DEVICE INCLUDING BIOMETRIC SENSOR

(71) Applicant: Samsung Electronics Co., Ltd., Gyeonggi-do (KR)

(72) Inventors: Seon-Ho Han, Suwon-si (KR); Tae-Gyun Kim, Seoul (KR); Jun-Hui Lee, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1482 days.

(21) Appl. No.: 15/792,903

(22) Filed: Oct. 25, 2017

(65) Prior Publication Data
US 2018/0116532 A1 May 3, 2018

(30) Foreign Application Priority Data
Oct. 28, 2016 (KR) .................. 10-2016-0142328

(51) Int. Cl.
A61B 5/026 (2006.01)
A61B 5/1455 (2006.01)
(Continued)

(52) U.S. Cl.
CPC .......... *A61B 5/0261* (2013.01); *A61B 5/0006* (2013.01); *A61B 5/1455* (2013.01);
(Continued)

(58) Field of Classification Search
CPC .... A61B 5/0261; A61B 5/0006; A61B 5/1455
See application file for complete search history.

(56) References Cited

U.S. PATENT DOCUMENTS 9,294,661 B2   3/2016  Choi et al.
9,310,843 B2*  4/2016  Shedletsky ......... H01L 51/5281
(Continued)

FOREIGN PATENT DOCUMENTS

CN   104765712 A   7/2015
CN   104820658 A   8/2015
(Continued)

OTHER PUBLICATIONS

International Search Report dated Jan. 29, 2018.
Chinese Search Report dated Aug. 26, 2021.
European Examination Report dated Dec. 1, 2022.

*Primary Examiner* — Alex M Valvis
*Assistant Examiner* — Yasmeen S Warsi
(74) *Attorney, Agent, or Firm* — Cha & Reiter, LLC

(57) ABSTRACT

An electronic device according to one embodiment of the present disclosure may include: a housing; an optical element unit which may be configured to emit light toward a user's body, receive light reflected from the user's body, and convert the received light into a first signal; an IC element which may be configured to convert the first signal provided from the optical element unit into a second signal, and provide the second signal to a main circuit board disposed in the housing; a first circuit board that may be disposed between the optical element unit and the IC element and may be electrically connected to the optical element unit and the IC element; and a second circuit board that may include at least one first opening in which the IC element is mounted. The housing may include at least one transparent region such that the light generated by the optical element unit is transmitted through the transparent region to an exterior of the housing.

18 Claims, 11 Drawing Sheets

(51) Int. Cl.
  *G06F 1/16* (2006.01)
  *A61B 5/00* (2006.01)
  *A61B 5/145* (2006.01)
  *A61B 5/0245* (2006.01)
  *A61B 5/024* (2006.01)
  *A61B 5/0205* (2006.01)
(52) U.S. Cl.
  CPC .............. *A61B 5/681* (2013.01); *G06F 1/163* (2013.01); *A61B 5/0205* (2013.01); *A61B 5/0245* (2013.01); *A61B 5/02416* (2013.01); *A61B 5/14532* (2013.01); *A61B 5/14551* (2013.01)

(56) References Cited

U.S. PATENT DOCUMENTS

| | | | |
|---|---|---|---|
| 2009/0194829 A1* | 8/2009 | Chung | B81C 1/00238 257/E23.181 |
| 2013/0069247 A1 | 3/2013 | Rahman et al. | |
| 2015/0265214 A1 | 9/2015 | De Kok et al. | |
| 2015/0282713 A1* | 10/2015 | Fei | A61B 5/6824 600/476 |
| 2016/0095218 A1* | 3/2016 | Sakurai | H05K 1/0218 361/768 |
| 2016/0105982 A1 | 4/2016 | Fuji | |
| 2016/0116609 A1* | 4/2016 | Cho | G01T 1/244 250/370.06 |
| 2016/0238439 A1* | 8/2016 | Chu | H01L 31/02327 |
| 2016/0242659 A1 | 8/2016 | Yamashita et al. | |
| 2016/0280539 A1 | 9/2016 | Ma et al. | |
| 2017/0045918 A1* | 2/2017 | Han | G06F 1/163 |
| 2019/0095218 A1 | 3/2019 | Subramanian et al. | |

FOREIGN PATENT DOCUMENTS

| | | | | |
|---|---|---|---|---|
| CN | 105286839 A | 2/2016 | | |
| CN | 105472863 A | 4/2016 | | |
| EP | 2 888 996 A1 | 7/2015 | | |
| JP | 2016-000205 A | 1/2016 | | |
| JP | 2016086873 A | 5/2016 | | |
| JP | 2016-147052 A | 8/2016 | | |
| JP | 2016-152911 A | 8/2016 | | |
| KR | 20150145650 A | * | 12/2015 | ........... A61B 5/1455 |
| KR | 1020150145650 A | 12/2015 | | |
| WO | 2016/071754 A2 | 5/2016 | | |

* cited by examiner

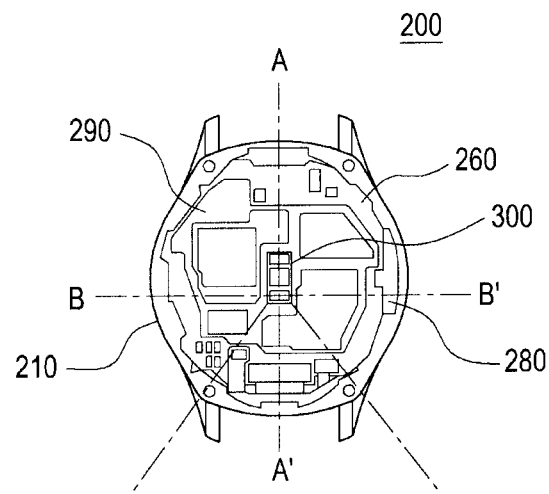
FIG.4A
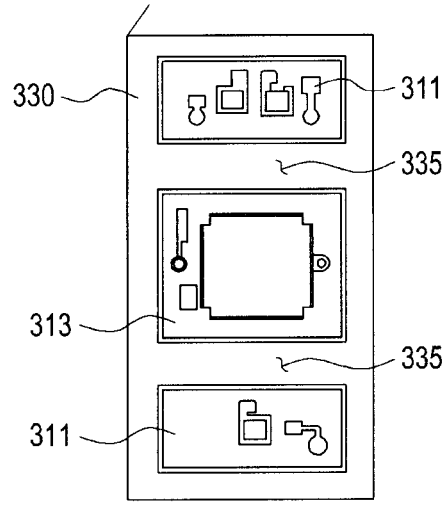 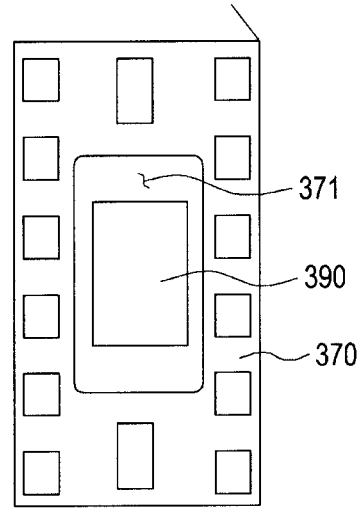
FIG.4B          FIG.4C

ELECTRONIC DEVICE INCLUDING BIOMETRIC SENSOR

CLAIM OF PRIORITY

This application claims the priority under 35 U.S.C. § 119(a) to Korean Patent Application Serial No. 10-2016-0142328, which was filed in the Korean Intellectual Property Office on Oct. 28, 2016, the entire content of which is hereby incorporated by reference.

TECHNICAL FIELD

Various embodiments of the present disclosure relate to an electronic device. Specifically, various embodiments of the present disclosure relate to an electronic device that includes a biometric sensor and a method of assembling the biometric sensor.

BACKGROUND

Electronic devices, such as electronic schedulers, portable multimedia players, mobile communication terminals, tablet PCs, desktop/laptop PCs, vehicular navigation systems, home appliances, etc., may be programmed to perform specific functions. For example, an electronic device may output information stored therein as text, sound or image As the degree of integration of these electronic devices has increased, and as super-high speed and large capacity wireless communication networks become more available, single mobile communication terminals are now designed to be capable of various functions. For example, a single mobile communication terminal may be capable of functions such as entertainment functions (e.g., gaming), multimedia functions (e.g., music/video playback), communication and security function for mobile banking, calendar function, and e-wallet function.

These portable electronic devices may be designed in various form factors, such as bar type, folder type, or sliding-type. Typically, the device also is equipped with one or more flat screen displays and one or more batteries. These devices may also be equipped with sensors. The sensors may collect information related to the electronic device, the environment of the electronic device, the user, etc. Various functions provided by electronic devices may use the information obtained by the sensors. Recently, as these electronic devices become increasingly more compact, wearable devices such as smart watches or head mounted devices have become increasingly more commercially available.

SUMMARY

Typically, biometric sensors known in the art are configured such that its photodiode is stacked on an IC element. In such a configuration, the size of the photodiode is generally smaller than that of the IC element. A relatively small photodiode may be disadvantageous because the amount of light detected by the photodiode is generally proportional to the size of the photodiode.

Further, when the photodiode and the IC element are implemented on the same plane in the biometric sensor, additional mounting spaces may be required for the photodiode and the IC element. This prevents the biometric sensor from being as compact as possible.

One embodiment of the present disclosure provides an electronic device that includes a sensor module where, for example, the size of the photodiode is not limited by the size of the IC element. This may be advantageous because it allows for better optical performance. In one embodiment, the photodiode and the IC element are mounted on the opposite sides of a circuit board disposed inside a biometric sensor module.

In addition, one or more embodiments of the present disclosure may also provide an electronic device that can be made more compact due to space savings in mounting the photodiode and the IC element as the ways as disclosed below According to one embodiment of the present disclosure, there is provided an electronic device that may include: a housing; an optical element unit which may be configured to emit light toward a user's body, receive light reflected from the user's body, and convert the received light into a first signal; an IC element which may be configured to convert the first signal provided from the optical element unit into a second signal, and provide the second signal to a main circuit board disposed in the housing; a first circuit board that may be disposed between the optical element unit and the IC element and may be electrically connected to the optical element unit and the IC element; and a second circuit board that may include at least one first opening in which the IC element is mounted. The housing may include at least one transparent region such that the light generated by the optical element unit is transmitted through the transparent region to an exterior of the housing.

According to one embodiment, there is provided an electronic device that may include: a housing; a biometric sensor module that may be disposed in the housing and may be configured to detect biometric information of a user; and a main circuit board that may be disposed adjacent to the biometric sensor module and may include at least one hole or groove. The biometric sensor module may include: an optical element unit; an IC element that may be inserted into the at least one hole or groove of the main circuit board, the IC element that may be configured to convert a signal provided from the optical element unit and provide the converted signal to the main circuit board; a first circuit board that may include a first face on which the optical element unit is disposed and a second face which is opposite the first face and on which the IC element is disposed; and a cover unit that may include at least one opening, such that the optical element unit is exposed toward the user's body.

According to one embodiment, there is provided a biometric sensor module disposed in an electronic device. The biometric sensor module may include: a first circuit board; an optical element unit that may be disposed on a front face of the first circuit board; an IC element that may be disposed on a rear face of the first circuit board; a cover unit that may be disposed on the front face of the first circuit board and may include at least one first opening such that the optical element unit is exposed toward a user's body; and a second circuit board that may be disposed on the rear face of the first circuit board and may include at least one second opening in which the IC element is mounted.

According to one embodiment, there is provided a method of assembling a biometric sensor module disposed in an electronic device. The method may include: providing a first circuit board configured to mount electronic components on both sides of the first circuit board; disposing an optical element unit on a front face of the first circuit board; disposing an IC element on a rear face of the first circuit board; disposing, on the front face of the first circuit board, a cover unit including at least one first opening such that the optical element is exposed toward a user's body; and disposing, on the rear face of the first circuit board, a second circuit board including at least one second opening in which the IC element is mounted.

According to one or more embodiments of the present disclosure, it is possible to provide an electronic device, in which the size of a photodiode can be enlarged by mounting a photodiode and an IC element on different faces of the circuit board disposed inside the biometric sensor module, thereby implementing a biometric sensor module that advantageously improves optical performance.

According to one or more embodiments of the present disclosure, it is possible to provide a slimmer electronic device in which the mounting spaces within the device are more efficiently utilized through various arrangements of the components of the biometric sensor module.

According to one or more embodiments of the present disclosure, it is possible to provide an electronic device where the biometric signal sensing sensor mounted therein comes into close contact with the user's body.

BRIEF DESCRIPTION OF THE DRAWINGS

The above and other aspects, features, and advantages of the present disclosure will be more apparent from the following detailed description taken in conjunction with the accompanying drawings, in which:

FIG. 4A is a view illustrating the position of an internal biometric sensor module 300 in the electronic device 200, according to one embodiment of the present disclosure;

FIG. 4B is an enlarged front view of the biometric sensor module 300 of FIG. 4A;

FIG. 4C is an enlarged rear view of the biometric sensor module 300 of FIG. 4A;

DETAILED DESCRIPTION

Figure 1:
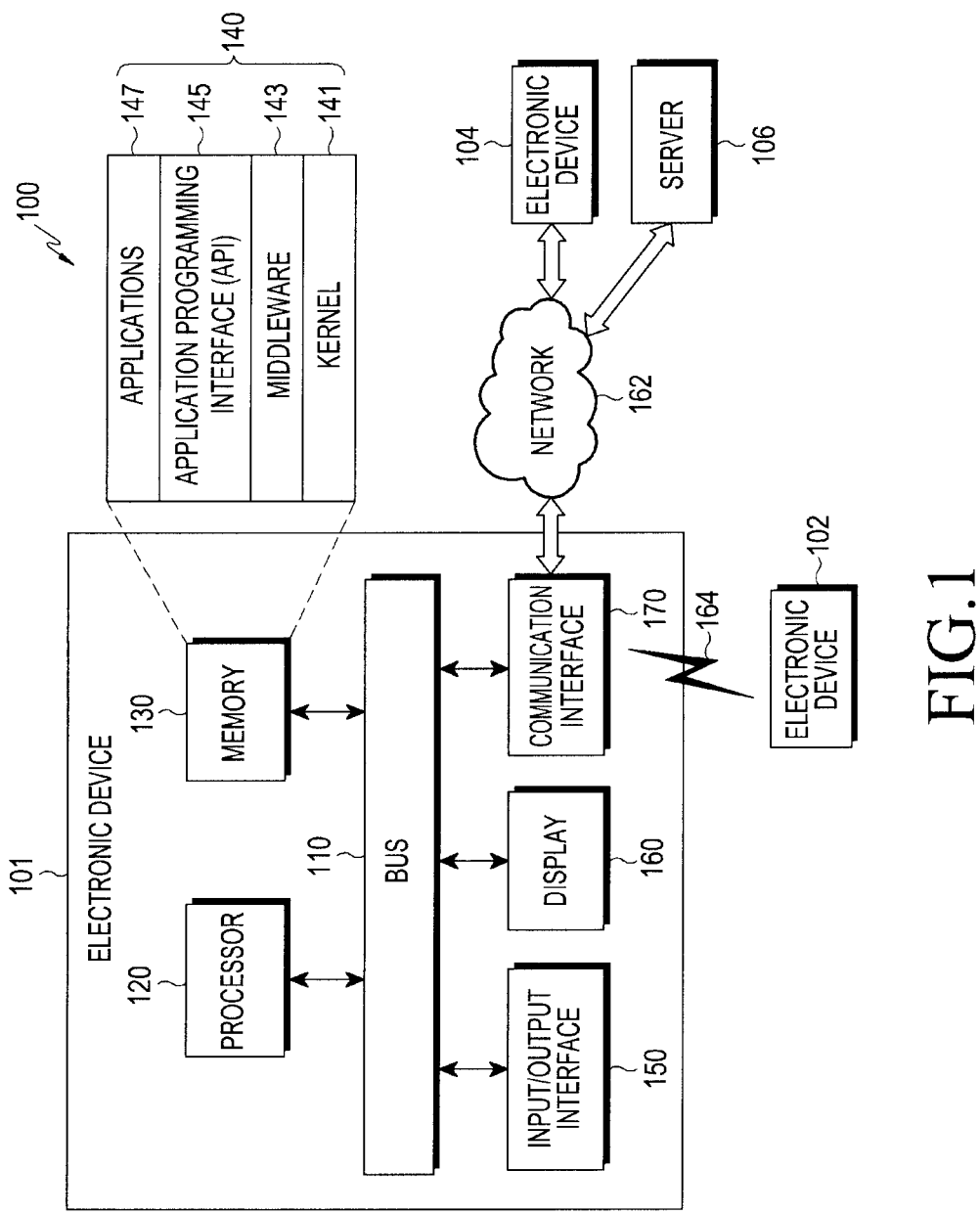
FIG. 1 is a schematic view illustrating an electronic device according to one embodiment within a network environment.

Hereinafter, various embodiments of the present disclosure will be described with reference to the accompanying drawings. However, the present disclosure is not intended to be limited by the disclosed embodiments and it is intended that the present disclosure covers all modifications, equivalents, and/or alternatives of the present disclosure provided they are within the scope of the appended claims and their equivalents. In the description of the drawings, similar reference numerals may be used to designate similar elements. The singular expression of "a," "an," and "the" include the plural thereof unless the context clearly indicates otherwise. The expression "a first", "a second", "the first", or "the second" used in various embodiments of the present disclosure may indicate various components regardless of the order and/or the importance and does not limit the corresponding components. In various embodiments of the present disclosure, it is intended that when a component (for example, a first component) is referred to as being "operatively or communicatively coupled with/to" or "connected to" another component (for example, a second component), the component may be directly connected to the other component or connected through another component (for example, a third component). In contrast, when a component (for example, a first component) is referred to as being "directly connected to" or "directly accessed by" another component (for example, a second component), another component (for example, a third component) does not exist between the component (for example, the first component) and the other component (for example, the second component).

The expression "configured to" used in various embodiments of the present disclosure may be interchangeably used with "suitable for," "having the capacity to," "designed to," "adapted to," "made to," or "capable of," depending on the context. The term "configured to" may not necessarily indicate "specifically designed to" in terms of hardware. Instead, the expression "a device configured to" in some situations may indicate that the device, alone or in conjunction with another device, are "capable of" For example, the expression "a processor configured to perform A, B, and C" may indicate a dedicated processor (for example, an embedded processor) for performing A, B, and C operations or a general purpose processor (for example, a central processing unit (CPU) or application processor (AP)) that performs A, B, and C by executing at least one software program stored in a corresponding memory device.

An electronic device according to various embodiments of the present disclosure may be a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, or a wearable device. The wearable device may be an accessory type device (e.g., a watch, a ring, a bracelet, an anklet, a necklace, a glasses, a contact lens, or a Head-Mounted Device (HMD)), a fabric or clothing integrated type device (e.g., an electronic clothing), a body-mounted type device (e.g., a skin pad, or tattoo), or a bio-implantable type device (e.g., an implantable circuit). In some embodiments, the electronic device may be, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV', or Google TV™), a game console (e.g., Xbox™ and PlayStation™), an electronic dictionary, an electronic key, a camcorder, or an electronic photo frame.

In other embodiments, the electronic device may be a medical device (e.g., a portable medical measuring device, such as a blood glucose monitoring device, a heart rate monitoring device, a blood pressure measuring device, a body temperature measuring device, etc., a Magnetic Resonance Angiography (MRA) device, a Magnetic Resonance Imaging (MRI) device, a Computed Tomography (CT) machine, or an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, a gyro-compass, etc.), avionics, security devices, an automotive head unit, a robot for home or industry, an Automatic Teller's Machine (ATM) in banks, Point Of Sales (POS) in a shop, or an Internet of Things (IoT) device (e.g., a light bulb, various sensors, electric or gas meter, a sprinkler device, a fire alarm, a thermostat, a streetlamp, a toaster, a sporting goods, a hot water tank, a heater, a boiler, etc.). According to some other embodiments, an electronic device may be a part of furniture or a building/structure, an electronic board, an electronic signature receiving device, a projector, or various types of measuring instruments (e.g., a water meter, an electric meter, a gas meter, a radio wave meter, and the like). The electronic device according to one embodiment may be flexible, or may be a combination of one or more of the aforementioned various devices. The electronic device according to the present disclosure is not limited to the above described devices. In the present disclosure, the term "user" may indicate a person using an electronic device or a device (e.g., an artificial intelligence electronic device) using an electronic device.

An electronic device 101 within the network environment 100 will be described with reference to FIG. 1. The electronic device 101 may include a bus 110, a processor 120, a memory 130, an input/output interface 150, a display 160, and a communication interface 170. In a certain embodiment, at least one of the above-mentioned components may be omitted from the electronic device 101 or the electronic device 101 may additionally include other components. The bus 110 may be a circuit that interconnects the above-mentioned components 110 to 170 and transfers communication information (e.g., a control message or data) among the components 110 to 170. The processor 120 may be a Central Processing Unit (CPU), an Application Processor (AP), or a Communication Processor (CP). The processor 120 may execute, for example, arithmetic operations or data processing that are related to the control and/or communication of one or more other components of the electronic device 101. The processor 120 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for." In addition, an artisan understands and appreciates that a "processor" or "microprocessor" may be hardware in the present disclosure. Under the broadest reasonable interpretation, the appended claims are statutory subject matter in compliance with 35 U.S.C. § 101.

The memory 130 may be a volatile memory and/or a non-volatile memory. The memory 130 may store, for example, commands or data that are related to one or more other components of the electronic device 101. According to one embodiment, the memory 130 may store software and/or a program 140. The program 140 may include, for example, kernel 141, middleware 143, Application Programming Interface (API) 145, and/or one or more application programs (or "application(s)" 147). At least one of the kernel 141, the middleware 143, and the API 145 may be referred to as an Operating System (OS). The kernel 141 may control or manage, for example, system resources (e.g., the bus 110, the processor 120, and the memory 130) that are used for executing operations or functions implemented in the other programs (e.g., the middleware 143, the API 145, or the application 147). In addition, the kernel 141 may provide an interface that allows the middleware 143, the API 145, or the application 147 to access individual components of the electronic device 101 so as to control or manage the system resources.

The middleware 143 may play an intermediary role such that, for example, the API 145 or the application 147 may communicate with the kernel 141 so as to exchange data. In addition, the middleware 143 may process one or more task requests which are received from the applications 147, according to a priority. For example, the middleware 143 may process the one or more task requests according to the priority, which makes it possible to perform scheduling or load balancing of the one or more task requests. The API 145 is, for example, an interface that allows the applications 147 to control functions provided from the kernel 141 or the middleware 143, and may include, for example, one or more interfaces or functions (e.g., commands) for a file control, a window control, an image processing, or a character control. The input/output interface 150 may transmit commands or data, which are entered from, for example, a user or any other external device, to the other component(s) of the electronic device 101, or may output commands or data, which are received from the other component(s) of the electronic device 101, to the user or the other external device.

The display device 160 may be a Liquid Crystal Display (LCD) display, a Light Emitting Diode (LED) display, an Organic Light Emitting Diode (OLED) display, a Micro-ElectroMechanical System (MEMS) display, or an electronic paper display. The display 160 may display various contents (e.g., text, image, video, icon, or symbol) to, for example, the user. The display 160 may include a touch screen, and may receive touch inputs, gesture inputs, proximity inputs, or hovering inputs that are made using, for example, an electronic pen or a part of the user's body. The communication interface 170 may set, for example, communication between the electronic device 101 and an external device (e.g., a first external electronic device 102, a second external device 104, or a server 106). For example, the communication interface 170 may be connected with a network 162 through wired or wireless communication so as to communicate with the external device (e.g., the second external electronic device 104 or the server 106).

The wireless communication may include a cellular communication that uses at least one of, for example, Long-Term Evolution (LTE), LTE Advance (LTE-A), Code Division Multiple Access (CDMA), Wideband CDMA (WCDMA), Universal Mobile Telecommunication System (UMTS), Wireless Broadband (WiBro), and Global System for Mobile communication (GSM). According to one embodiment, the wireless communication may include at least one of, for example, Wireless Fidelity (WiFi), Bluetooth, Bluetooth Low Energy (BLE), ZigBee, Near Field Communication (NFC), Magnetic Secure Transmission, Radio Frequency (RF), and Body Area Network (BAN). According to one embodiment, the wireless communication may include GNSS. The GNSS may include, for example, at least one of Global Positioning System (GPS), Global Navigation Satellite System (Glonass), Beidou Navigation Satellite System (hereinafter, "Beidou"), Galileo, and the European global satellite-based navigation system, according to, for example, a use area or band width. Herein, "GPS" may be interchangeably used with "GNSS" below. The wired communication may use at least one of, for example, Universal Serial Bus (USB), High Definition Multimedia Interface (HDMI), Recommended Standard 232 (RS-232), and Plain Old Telephone Service (POTS). The network 162 may include a telecommunication network (e.g., at least one of a computer network (e.g., LAN or WAN), the internet, and a telephone network).

Each of the first and second external electronic devices 102 and 104 may be the same type as or different from the electronic device 101. According to various embodiments, all or some of the operations to be executed by the electronic device 101 may be executed in another electronic device or a plurality of other electronic devices (e.g., the external electronic devices 102 and 104 or the server 106). According to one embodiment, in the case where the electronic device 101 should perform a certain function or service automatically or by a request, the electronic device 101 may request some functions or services that are associated therewith from the other electronic devices (e.g., the external electronic devices 102 and 104 or the server 106), instead of, or in addition to, executing the functions or service by itself. The other electronic devices (e.g., the external electronic devices 102 and 104 or the server 106) may execute the requested functions or additional functions, and may deliver the results to the electronic device 101. The electronic device 101 may provide the requested function or service using the received result or may additionally process the received result to provide the requested function or service. For this purpose, for example, cloud computing techniques, distributed computing techniques, or client-server computing techniques may be used.

Figures 2A, 2B:
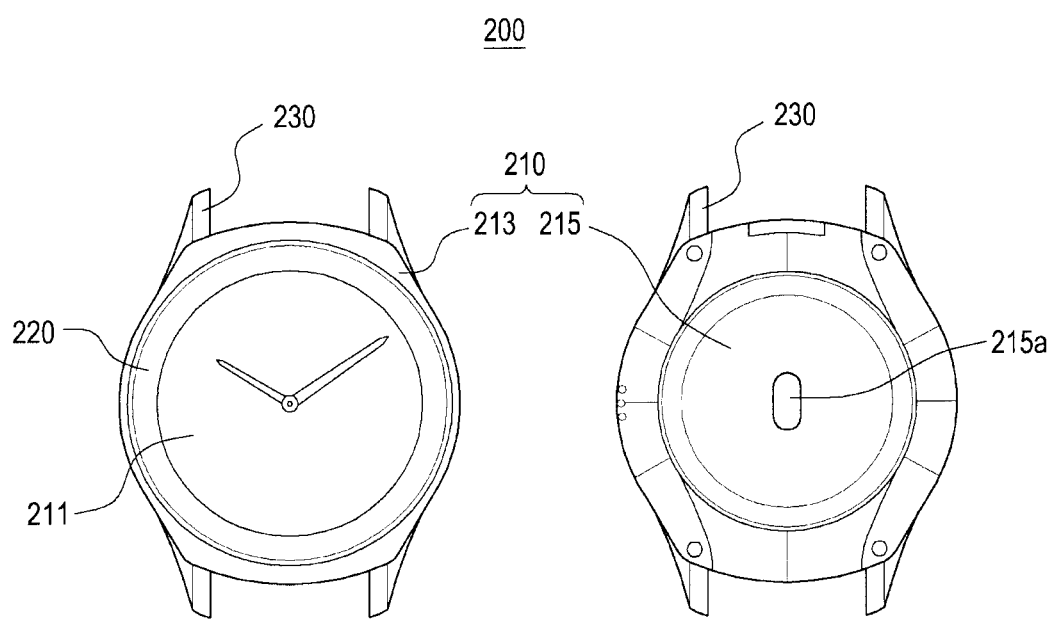
FIG. 2A is a front view illustrating an electronic device 200 according to one embodiment of the present disclosure.
FIG. 2B is a rear view illustrating the electronic device 200 according to one embodiment of the present disclosure.

FIG. 2A is a front view illustrating an electronic device 200 according to one embodiment of the present disclosure. FIG. 2B is a rear view illustrating the electronic device 200 according to one embodiment of the present disclosure.

An electronic device according to various embodiments of the present disclosure may be a portable electronic device, such as a mobile communication terminal, or a wearable electronic device that is worn on the user's body. For illustration purposes only, an example of a smart watch is used in the below descriptions. However, the present disclosure is not limited to smart watches.

Referring to FIGS. 2A and 2B, the electronic device 200 includes a housing 210 including a transparent plate 211, a bezel 220, and detachable portions 230. The "first direction" used for describing various embodiments of the present disclosure indicates a direction perpendicular to and extending outward from the transparent plate 211. Conversely, the "second direction" is a direction opposite the "first direction."

According to one embodiment, the housing 210 may include a first face 213 facing the first direction and a second face 215 facing the second direction. The front face of the housing 210 may include an opening, and the transparent plate 211 may be mounted in the opening to form a portion of the first face 213. The second face 215 of the housing 210 may include at least one transparent region 215a so that light generated in an optical element unit disposed inside the housing is emitted to the exterior of the housing 210.

Various circuit devices, such as a processor 120 (e.g., an application processor (AP) described above with reference to FIG. 1), a memory 130, an input/output interface 150, a communication interface 170, and so on may be accommodated in the housing 210, and the power for these circuit devices can be supplied by a battery (not shown) also accommodated in the housing 210.

According to one embodiment, the housing 210 may be made of metal. For example, a portion (e.g., the rim) of the housing 210 may be made of metal, and the remaining portion of the housing 210 may be made of plastic.

According to one embodiment, the transparent plate 211 may be made of a transparent material, such as glass or a resin (e.g., acrylic or polycarbonate). This way, the transparent plate 211 provides a window so that the display device (the display 160 of FIG. 1) of the electronic device 200 is visible. For example, the display device may output a screen showing an analog clock through the transparent plate 211.

According to one embodiment, the bezel 220 may be disposed at the rim of the transparent plate 211. The bezel 220 may be rotatably coupled with the housing 210 so that it can rotate along the rim of the transparent plate 211 relative to the housing 210. For aesthetic reasons, the bezel 220 may be made of metal. However, when the bezel 220 is made of metal, the bezel 220 can also be functionally used as an antenna radiator.

According to one embodiment, the detachable portions 230 may extend and protrude from the opposite ends of the housing 210 in directions away from each other. The detachable portions 230 may be coupled with wearing units (not shown) to enable wearing of the electronic device 200 on the user's wrist. The detachable portions 230 are formed with fastening grooves that receive the wearing units. The wearing units may be made of various materials such as rubber, plastic, metal, etc. If the user wishes to alter the appearance of the electronic device 200, different wearing units may be attached to/detached from the detachable portions 230 of the electronic device 200.

Figure 3:
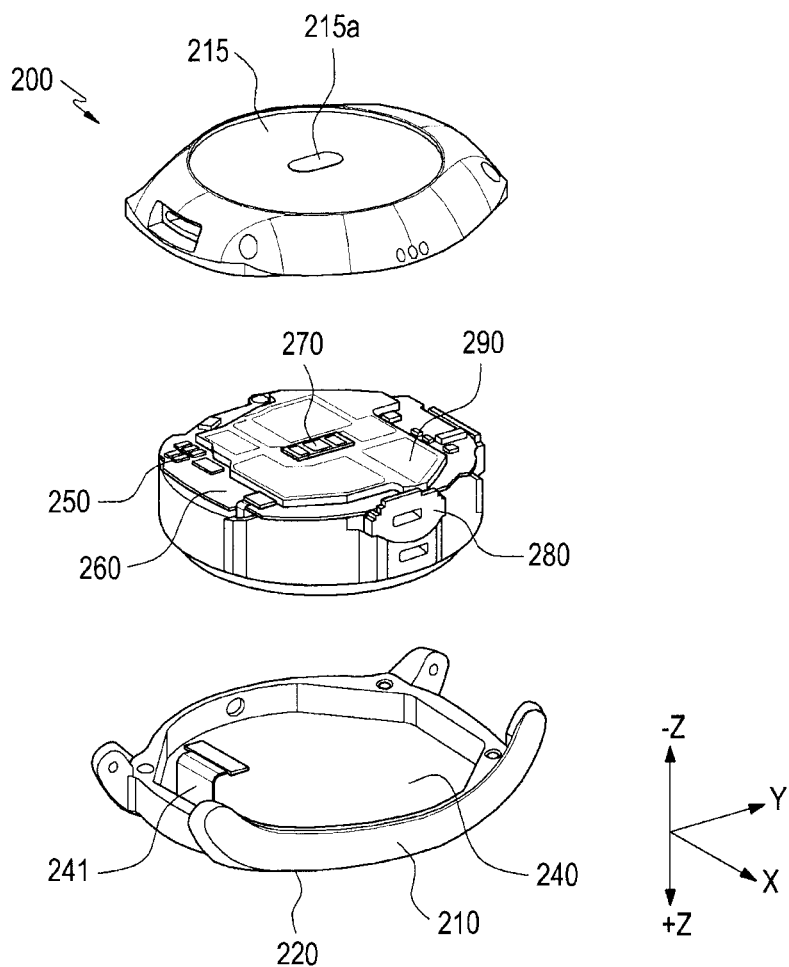
FIG. 3 is an exploded perspective view illustrating the internal structure of the electronic device 200 according to one embodiment of the present disclosure.

FIG. 3 is an exploded perspective view illustrating the internal structure of the electronic device 200 according to one embodiment of the present disclosure. In FIG. 3, an orthogonal coordinate system of three axes is shown. The "X-axis" may correspond to the width direction of the electronic device 200, the "Y-axis" may correspond to the length direction of the electronic device 200, and the "Z-axis" may correspond to the thickness direction of the electronic device 200.

Referring to FIG. 3, in one embodiment, the electronic device 200 includes a housing 210, a bezel 220, a display device 240, an electronic component 250, a main circuit board 260, a bracket 280, a battery, and a biometric sensor 270. The structure of the housing 210 and/or the bezel 220 of the electronic device 200 illustrated in FIG. 3 may correspond to the structure of the housing 210 and/or the bezel 220 illustrated in FIG. 2.

According to one embodiment, the housing 210 may accommodate various electronic components including, for example, the display device 240, the main circuit board 260, the electronic component 250, and the biometric sensor 270. A portion of the housing 210, for example, the side face of the housing 210, may be at least partially made of a material that permits transmission of electromagnetic signals.

According to one embodiment, the display device 240 may be coupled in the second direction (−Z) with respect to the transparent plate (the transparent plate 211 in FIG. 2). The display device 240 may display image information (e.g., text, image, video) through the transparent plate 211. The display device 240 may also output executing screens for various applications of the electronic device 200 (e.g., games, internet banking apps, and calendar apps) according to the user's operation.

The display device 240 may be a Liquid Crystal Display (LCD) display, a Light-Emitting Diode (LED) display, an Organic Light-Emitting Diode (OLED) display, a Micro-ElectroMechanical System (MEMS) display, an electronic paper display, etc. The display device 240 may include a touch screen panel integrated therewith to perform ouch detection. In one embodiment, the display device 240 may have an antenna radiator mounted on its inner or outer face thereof to enable wireless signal transmission or reception.

The display device 240 may be electrically connected to the display circuit board 241. The display circuit board 241 may be disposed inside the housing 210. The display circuit board 241 may transmit electrical signals for driving the display device 240.

According to one embodiment, the main circuit board 260 may be disposed to be adjacent to a battery (not shown). On the main circuit board 260, processors, communication modules and the like may be mounted as an integrated circuit chip. The main circuit board 260 may be electrically connected to the battery. The main circuit board 260 may be electrically connected to the electronic part 250 by a connector.

According to one embodiment, the electronic component 250 may be disposed on the main circuit board 260, and may include an antenna radiator and/or a wireless charging antenna. For example, the antenna radiator may be a Magnetic Security Transmission (MST) antenna. As another example, the antenna radiator may be a Near-Field Communication (NFC) antenna. A shielding structure may be disposed around the antenna radiator to prevent signal interference between the antenna radiator and the other electronic components.

According to one embodiment, the wireless charging antenna may be attached to one face of the main circuit board 260. The wireless charging antenna may be in the shape of a flat coil. The wireless charging antenna may be conductive, and may be electrically connected to the main circuit board 260. The wireless charging antenna may generate current by electromagnetic induction generated from an external electronic device, such as an external charging device. The current generated in the wireless charging antenna may charge the battery (not shown).

According to one embodiment, a heat dissipation structure (not shown) may be provided between the main circuit board 260 and the battery. For example, the heat dissipation structure may dissipate heat generated from the main circuit board 260, thereby preventing the main circuit board 260 from being overheated. A shielding structure 290 may be disposed between the main circuit board 260 and the second side 215. The shielding structure 290 may be disposed in a space between the electronic components on the main circuit board 260 and the biometric sensor 270 in order to prevent mutual interference therebetween.

The second face 215 formed in the second direction (−Z) on the housing 210 may form a rear cover of the housing 210. The rear cover may be made of glass. The rear cover may come into contact with a portion of the user's body (e.g., a wrist). In one embodiment, the rear cover may be made of a transparent material, such as transparent reinforced plastic or glass. For example, the center region of the rear cover may be made of a transparent plate to enable sensing operations of the biometric sensor 270, and the other region of the rear cover may be opaque. In other words, the rear cover may include at least one transparent region 215a so that light generated from an optical element of the biometric sensor 270 may be emitted onto the user's body.

The biometric sensor 270 may be disposed between the main circuit board 260 and the second face 215 to detect biometric information of the user. For example, the biometric sensor 270 may include a Heart Rate Monitor (HRM) that detects the heartrate of the user. By detecting light reflected from the user's body, the HRM may detect vessel contraction/expansion of the user's blood vessels. The HRM may then generate electrical signals in accordance with the detected vessel contraction/expansion. The processor (e.g., the processor 120 of FIG. 1) may then receive the electrical signals from the biometric sensor 270 to calculate heartbeat.

FIG. 4A is a view illustrating the position of an internal biometric sensor module 300 in the electronic device 200, according to one embodiment of the present disclosure. FIG. 4B is an enlarged front view of a biometric sensor module 300 of FIG. 4A, and FIG. 4C is an enlarged rear view of the biometric sensor module 300 of FIG. 4A.

Figure 5A:
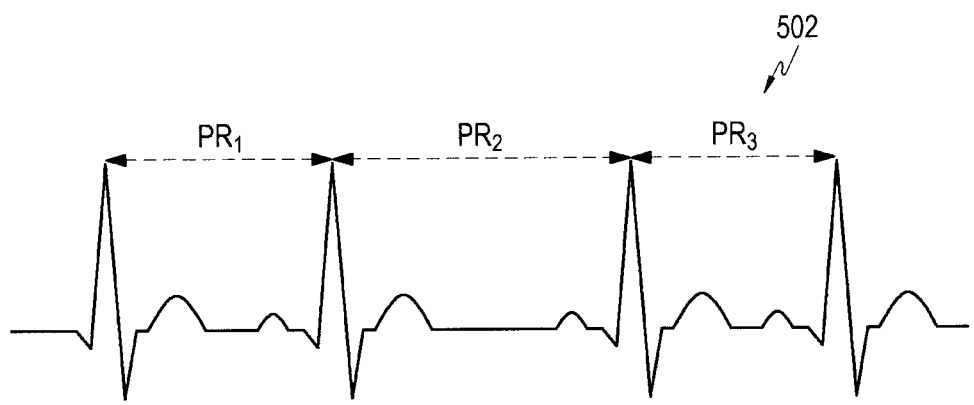
FIG. 5A and FIG. 5B are graphs illustrating an electrocardiogram (ECG) waveform and a heartbeat waveform detected by the biometric sensor module 300 according to one embodiment of the present disclosure in comparison.
Figure 5B:
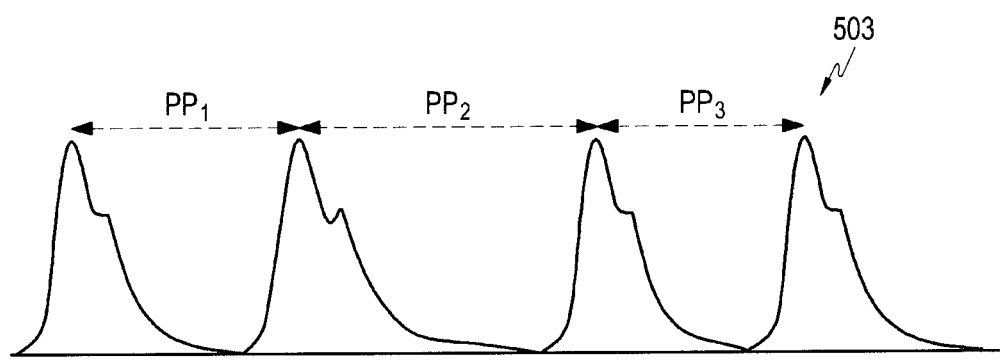
Figure 6:
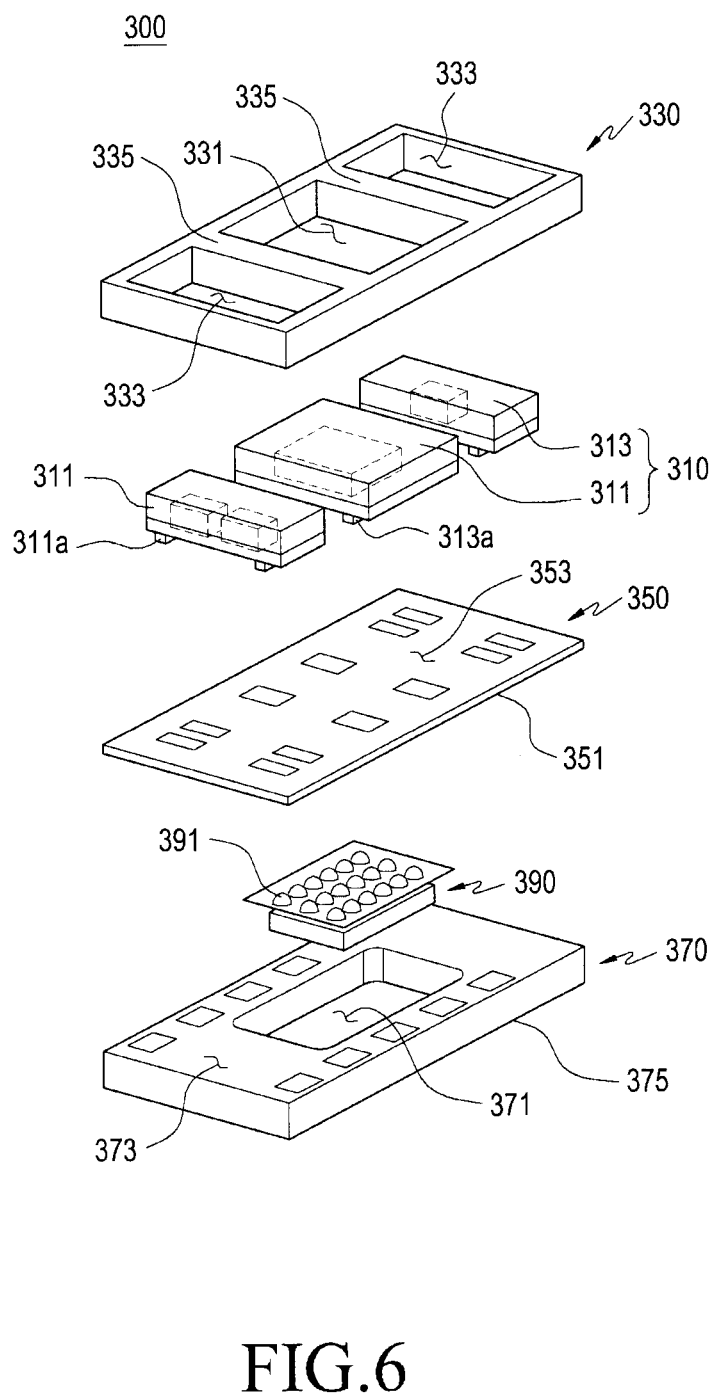
FIG. 6 is an exploded perspective view illustrating the internal configuration of the biometric sensor module 300 according to one embodiment of the present disclosure.

FIGS. 5A and 5B are graphs illustrating an ECG waveform and a heartbeat waveform detected by the biometric sensor module 300 according to one embodiment of the present disclosure in comparison. FIG. 6 is an exploded perspective view illustrating the internal configuration of the biometric sensor module 300 according to one embodiment of the present disclosure.

Referring to FIGS. 4 and 6, the electronic device 200 according to one embodiment of the present disclosure may include a housing 210, a main circuit board 260, and/or a biometric sensor module 300. The structure of the housing 210, the main circuit board 260, and/or the biometric sensor module 300 of the electronic device 200 illustrated in FIG. 4 or 6 may correspond to that of the housing 210, the main circuit board 260, and/or the biometric sensor module 270 illustrated in FIG. 3.

In one embodiment, the biometric sensor module 300 may be disposed to face the rear face of the electronic device 200. For example, the biometric sensor module 300 may be arranged to be in close contact the second face 353 of the housing 210 that comes into contact with the user's body, so that the biometric sensor module 300 is as close to the skin as possible to optimize biometric detection operations.

The biometric sensor module 300 may be disposed on the main circuit board 260, and may be electrically connected to the main circuit board 260. A shielding structure 290 may be disposed around the biometric sensor module 300 to shield other electronic components of the main circuit board 260 from the biometric sensor module 300 and vice versa. FIG. 4B is a view in the second (−Z) direction of the biometric sensor module 300. As shown in FIG. 4B, as viewed from the second direction, a photodiode 313 may be disposed at the center and one or more light sources 311 may be disposed around the photodiode 313. FIG. 4C is a view in the first (+Z) direction of the biometric sensor module 300. As viewed from the first direction, an IC element 390 may be disposed at the center of the biometric sensor module 300.

According to one embodiment, the biometric sensor module 300 may be disposed between the main circuit board 260 and the second face 353 to sense biometric information of the user. The biometric sensor module may be, for example, a sensor that collects or measures one or more biometric signals from the user. The biometric sensor module may collect raw data for measuring one or more of the user's blood pressure, blood flow, heart rate (heart rate or heart rate variability (HRV)), body temperature, respiration rate, oxygen saturation, cardiac tone, blood sugar, waist size, height, weight, body fat, calorie consumption, brainwaves, voice, skin resistance, electromyogram, electrocardiogram, gait, sleep state, facial expression, pupil dilation, eye blinking, etc.

The electronic device may generate biometric information by analyzing a biometric signal. For example, a pulse wave signal may be generated by a HRV or HRM sensor. The electronic device may obtain primary biometric information such as average heart rate or heart rate distribution by analyzing the pulse wave signal. The electronic device may also obtain secondary biometric information, such as stress state of the user or vascular aging by processing the biometric information.

According to one embodiment, the biometric sensor module may simply output the collected user's biometric signals, or may output biometric information by analyzing the biometric signals through a built-in processor. Therefore, the biometric signals collected through the biometric sensor module may be transmitted to a processor within the biometric sensor module, the processor of the electronic device having the biometric sensor module embedded therein, or the processor of an external device (e.g., the server 106 or the electronic device 104 in FIG. 1).

When the electronic device 200 having the biometric sensor module embedded therein transmits a biometric signal to a remote device (e.g., the electronic device 104 of FIG. 1) or a server (e.g., the server 106 in FIG. 1), the remote device or the server that receives the biometric signal may process the biometric signal to generate biometric information. Alternatively, when the electronic device 200 generates primary biometric information, it may transmit the generated biometric information to a remote device or a server, and the remote device or the server may generate the secondary biometric information.

For example, the biometric signals collected by an HRM sensor or an HRV sensor embedded in a wristwatch device (an example of a wearable device) may be transmitted to a smartphone (an example of a host or main electronic device) wirelessly connected to a wristwatch device. The smartphone may analyze the received biometric signals so as to generate biometric information. The biometric information may be displayed on the display of the smartphone or displayed on the display of the wristwatch device. The biometric information may be displayed or stored on one or both of the smartphone and the wristwatch device. According to another embodiment, the biometric signals may be collected by an HRM sensor or an HRV sensor embedded in an ear clip of an earphone, and the biometric signals may be transmitted to connected wristwatch device or smartphone. The wristwatch device or the smartphone may then generate biometric information. The generated biometric information may be delivered to one or more other devices. When the biometric information is generated in the smartphone, the wristwatch device that receives the biometric information may display the biometric information. Alternatively, the connected earphone may output the biometric information using a text-to-voice conversion module FIGS. 5A and 5B are graphs illustrating an ECG waveform and a heartbeat waveform. FIG. 5A shows an ECG waveform 502, and FIG. 5B shows a heartbeat waveform 503. With respect to the respective waveforms in FIGS. 5A and 5B, the horizontal axis represents time and the vertical axis represents the intensity of current or voltage. Heart rate sensor are also referred to as pulse sensors or pulse wave sensors. In one embodiment of the present disclosure, the heart rate sensor of the biometric sensor module includes a Heart Rate Monitor (HRM) capable of measuring heart rate per unit time and a sensor capable of measuring Heart Rate Variability (HRV), which is the variation of time intervals between heartbeats. The heart rate or HRV may be obtained not only based on an ECG; but also via a heart rate sensor. For example, the heartrate may be determined using the peak values shown in the heartbeat waveform 503. Although there is a slight time difference between the peak of the ECG waveform 502 and the heartbeat waveform 503, the inter-peak distances PR1, PR2, and PR3 of the ECG waveform 502 and the inter-peak distances PP1, PP2, and PP3 of the heartbeat waveform 503 are very similar to each other. This fact may be found from various documents including the "A comparative analysis of heart rate variability of Electrocardiogram and Pulse-wave using time series," Naghwan Kim, et al., Journal of Korean Soc Med Inform. 2000 December; 6(4); 165-173.

According to one embodiment, as the heart contracts and relaxes, the blood flow in a peripheral blood vessel may change, and the volume of the blood vessel may also change. A photoplethysmography (PPG) sensor is a sensor that measures the amount of light transmitted through an organ, such as blood vessels. The PPG can be used to measure the change in the amount of blood in the blood vessel or oxygen saturation of the vessel.

Thus, in one embodiment, the heartbeat sensor may be embedded in a clip, a wristwatch, a necklace, a band, a mobile phone, etc., and may measure heart beat when the heartbeat sensor is in contact with a portion of the user's body. For example, when measurement is performed using a finger, when the finger is brought into contact with the heartbeat sensor, the heartbeat sensor measures a change in the amount of light transmitted through the finger to determine the heartbeat. For example, in the contraction phase, blood increases in the vessels of the finger so that the amount of light transmitted through the finger is relatively small. But in the relaxation phase, blood is released from the vessels of the finger, and the amount of light transmitted through the finger is relatively large.

The heartbeat sensor may detect the amount of light as a voltage, and the heartbeat sensor or the electronic device may convert the detected voltage into a digital value, thereby measuring the frequency of occurrence of heartbeats. The heartbeat sensor or electronic device may determine how many pulses are generated per second based on the detected voltage, and may calculate a heart rate or an elapsed time between heart beats based thereon. When the PPG sensor is embedded in a wristwatch, biomedical signals may be detected through the radial artery or the ulnar artery, and vital signals may be measured through a portion of the user's body where blood vessels are distributed even if the blood vessels are not necessarily the arteries. In addition, there may be a time difference between the ECG signal and the heartbeat signal because there is a delay in delivering the signals from the heart to respective portions of the human body. For example, when a heartbeat sensor is mounted in a wristwatch or an ear clip, a time delay may occur because blood requires time to flow from the heart to the wrist or ear.

Depending on age, heart rate per minute varies, and heart rate pattern varies according to for example, the health condition or the emotional state of the user. The electronic device 200 may measure blood vessel elasticity through pulse wave analysis, and may determine blood vessel age. The electronic device may also analyze the intensity of the heartbeat output, the blood vessel elasticity, and the residual blood volume through an Accelerated PhotoplethysmoGraphy (APG) analysis of the pulse wave signals detected by the biometric sensor module 300. Through this, tests of hypertension, diabetes, hyperlipidemia, arteriosclerosis, heart disease, peripheral blood circulation disorder, etc. may be performed by automatically analyzing blood vessel elasticity, blood vessel hardness, etc.

Referring again to FIGS. 4 and 6, when the biometric sensor module 300 is viewed from the outside of the electronic device 200, a cover unit 330, a first circuit board 350, and the second circuit board 370 may be sequentially stacked inwardly from the outside (e.g., in the first (+Z) direction). An optical element unit 310 may be disposed inside the cover unit 330 and an IC element 390 may be disposed inside the second circuit board 370. Accordingly, the optical element unit 310, the first circuit board 350, and the IC element 390 may be sequentially stacked inwardly from the outside (e.g., in the first (+Z) direction).

According to one embodiment, the optical element unit 310 may be disposed on the first circuit board 350 to face the second (−Z) direction. The optical element unit 310 may emit light toward the user's body, and may receive the light reflected from the user's body. The optical element unit 310 may include one or more light sources 311 and photodiode 313. Various arrangements of the one or more light sources 311 and the photodiode 313 are possible.

For example, the one or more light sources 311 and the photodiode 313 may be disposed on the same plane. In this way, the photodiode 313, which is electrically connected to a first circuit board 350, may be disposed on the second face 353 of the first circuit board 350. The plurality of light sources 311 may be disposed such that the photodiode 313 is spaced apart from the light sources 311 and is interposed between the light sources 311. The plurality of light sources 311 may be disposed on the second face 353 of the first circuit board 350, and may be electrically connected to the first circuit board 350.

The one or more light sources 311 may emit light in the second (−Z) direction. For example, the light source 311 may be an LED module capable of emitting light of various colors. The emitted light may have a wavelength in the range of about 380 nm to 800 nm. As another example, the light emitted from the light source 311 may be green light, and may have a wavelength in the range of about 450 nm to 600 nm. The light source 311 may be configured to include a cap that caps its internal circuits that emit light, and the capping material may be, for example, epoxy. At least one pad 311a connected to the internal circuits of the light source 311 may be disposed on the lower end of the light source 311 in order to electrically connect the light source 311 to the first circuit board 350.

According to one embodiment, when the light emitted from the light source 311 is reflected by the user's body, the photodiode 313 may receive the reflected light and may convert the light into current. For example, when a part of the light emitted from the light source 311 is reflected by the blood flow in the blood vessel of the user, the photodiode 313 may convert the reflected light into a current signal. As another example, since the photodiode 313 should have a large surface area in order to sufficiently receive the reflected light, the photodiode 313 may be formed to be wider than the IC element, for example the IC element 390, disposed therebelow.

According to one embodiment, the cover unit 330 may be stacked on the first circuit board 350, and may include one or more openings 331 and 333 to receive the photodiode 313 and light source 311. The cover unit 330 may also have one or more walls 335 separating the photodiode 313 and light source 311 to prevent mutual signal interference between the photodiode and the light sources.

For example, the cover unit 330 may have a plate shape including a plurality of openings 331 and 333, and the openings 331 and 333 may penetrate the upper and lower faces of the cover unit 330. The plurality of openings 331 and 333 may include a first opening 331 and one or more second openings 333 having sizes different from that of the first opening 331.

Referring to FIG. 4B, when viewed in the first (+Z) direction, the first opening 331 may be disposed at the center of the cover unit 330, and the plurality of second openings 333 may be disposed on either side of the first opening 331. For example, the photodiode 313 may be disposed at the center of the first circuit board 350 may be exposed through the first opening 331 in the second (−Z) direction. Likewise, the light sources 311 are disposed on the opposite sides of the first circuit board 350 may be exposed through the second openings 333 in the second (−Z) direction.

According to one embodiment, between the first opening 331 and the second opening 333 of the cover unit 330, one or more walls 335 may be formed to define the openings. The light emitted from the light source 311 should be directly transmitted to the user, and the light reflected by the user should be transmitted to the photodiodes 313. The walls 335 cut off direct paths through which the light emitted from the light source 311 may be received by the photodiode 313. Accordingly, the walls 335 prevent optical interference between the light source 311 and to the photodiode 313.

The first opening 331 of the cover unit 330 may be formed in a shape corresponding to the shape of the photodiode 313, and the second openings 333 of the cover unit 330 may be formed in shapes corresponding to the shapes of the light sources 311. For example, the first opening 331 and/or the second openings 333 may be formed in the form of a square hole, and the size of the first opening 331 may be relatively larger than that of the second openings 333. As another example, one first opening 331 may be formed at the center of the cover unit 330, and two second openings 333 may be formed at the opposite sides of the first opening 331. As another example, the thickness of the first opening 331 and the second openings 333 of the cover unit 330 may be longer than the thickness of the light sources 311 and the photodiode 313. Although the number and shape of the first opening 331 and the second openings 333 are disclosed according to an embodiment of the present disclosure, but the present disclosure is not limited to the number and shape of the first opening 331 and the second openings 333. The first opening 331 and the second openings 3 may be variously modified in number and shape to correspond to the light sources and the photodiode.

According to one embodiment, the first circuit board 350 may include a first face 351 facing the first (+Z) direction and a second face 353 facing the second (−Z) direction opposite the first (+Z) direction.

The first circuit board 350 may be in the form of a plate. To efficiently mount components, one or more electronic elements may be mounted on both the first face 351 and the second face 353. According to one embodiment, an IC element 390 may be disposed on the first face 351 of the first circuit board 350 and electrically connected to the first circuit board 350. For example, the IC element 390 may be disposed in the central region of the first face 351 of the first circuit board 350, and may include at least one pad 391 disposed on the lower end thereof to electrically connect to the first face 351.

According to one embodiment, the optical element unit 310 may be disposed on the second face 353 of the first circuit board 350 and electrically connected to the first circuit board 350. For example, the photodiode 313 of the optical element unit 310 may be disposed in the central region of the second face 353 of the first circuit board 350, and a pad 313a disposed on the lower end of the photodiode 313 electrically connects the photodiode 313 to the second face 353. In addition, the one or more light sources 311 of the optical element unit 310 may be disposed in an edge region of the second face 353 of the first circuit board 350, and pads 311a disposed on the lower ends of the light sources 311 may electrically connect the light sources 311 to the second face 353.

According to one embodiment of the present disclosure, the photodiode 313 and the IC element 390 may be separated into separate components disposed on opposite sides of the first circuit board 350, rather than being integrally formed. This way, the size of the photodiode 313 does not have to equal to that of the IC element 390. For example, if a relatively large photodiode 313 compared with the IC element 390 is arranged on the first circuit board 350, it is possible to ensure a wide light receiving area for the photodiode 313, which may enable the photodiode 313 to detect more accurate biometric signals.

In addition, the electronic elements of the biometric sensor module 300 may be disposed on the opposite faces of the first circuit board 350 so that space within the electronic device can be more efficiently used.

According to one embodiment, the first circuit board 350 may be manufactured such that its size of the first face 351 and/or the second face 353 is the same as the size of the second circuit board 370 and/or the cover unit 330. Accordingly, the biometric sensor module 300 may be formed in a substantially rectangular shape, and may be appropriately disposed in the internal space of the housing 210 of the electronic device. However, the structure of the biometric sensor module 300 is not so limited thereto.

According to one embodiment, the IC element 390 may be disposed on the first face 351 of the first circuit board 350 and may convert a current signal transmitted from the optical element unit 310 into a voltage signal.

One face of the IC element 390 may be disposed opposite the photodiode 313 with the first circuit board 350 being interposed therebetween, and the other face of the IC element 390 may be exposed to the outside of the biometric sensor module 300 so as to be connected to the main circuit board 260 of the device 200. For example, the IC element 390 may be disposed inside the second circuit board 370 and exposed through the third opening 371 of the second circuit board 370 in a first (+Z) direction.

One or more pads connected to the internal circuitry of the IC element 390 may be disposed on one face of the IC element 390 to be electrically connected to the first circuit board 350. The IC element 390 may be an analog front-end IC. Hereinafter, a procedure of operating the internal circuitry of the IC element 390 will be described in detail.

In one embodiment, the second circuit board 370 may be disposed to face the first circuit board 350. The second circuit board 370 may be manufactured in a plate shape, and may form the external structure of the biometric sensor module 300. The second circuit board 370 may include a first face 373 facing the second (−Z) direction and a second face 375 facing the first (+Z) direction. As another example, the second circuit board 370 may include a third opening 371 that penetrates the first face 373 and the second face 375.

At least one electronic element may be disposed inside the third opening 371 of the second circuit board 370, so that a mounting space may be efficiently utilized. For example, the IC element 390 disposed on the first circuit board 350 may be accommodated inside the third opening 371, and the IC element 390 disposed inside the third opening 371 may be exposed to face the first (+Z) direction.

The third opening 371 of the second circuit board 370 may be configured to correspond to the shape of the IC element 390. For example, when the IC element 390 is substantially square, the third opening 371 may be formed in the shape of a square hole, and may be disposed at the center of the second circuit board 370. As another example, the thickness of the third opening 371 of the second circuit board 370 may be greater than the thickness of the IC element 390. Although the number and shape of the third openings 371 are disclosed according to one example of the present disclosure, the present disclosure is not so limited.

According to one embodiment, one or more pads may be formed on the first face 373 of the second circuit board 370 to face the second (−Z) direction, and may be electrically connected to the first circuit board 350. Also, one or more pads may be formed on the second face 375 of the second circuit board 370 to face the first (+Z) direction, and may be electrically connected to a main circuit board 260 within the electronic device 200.

Figure 7:
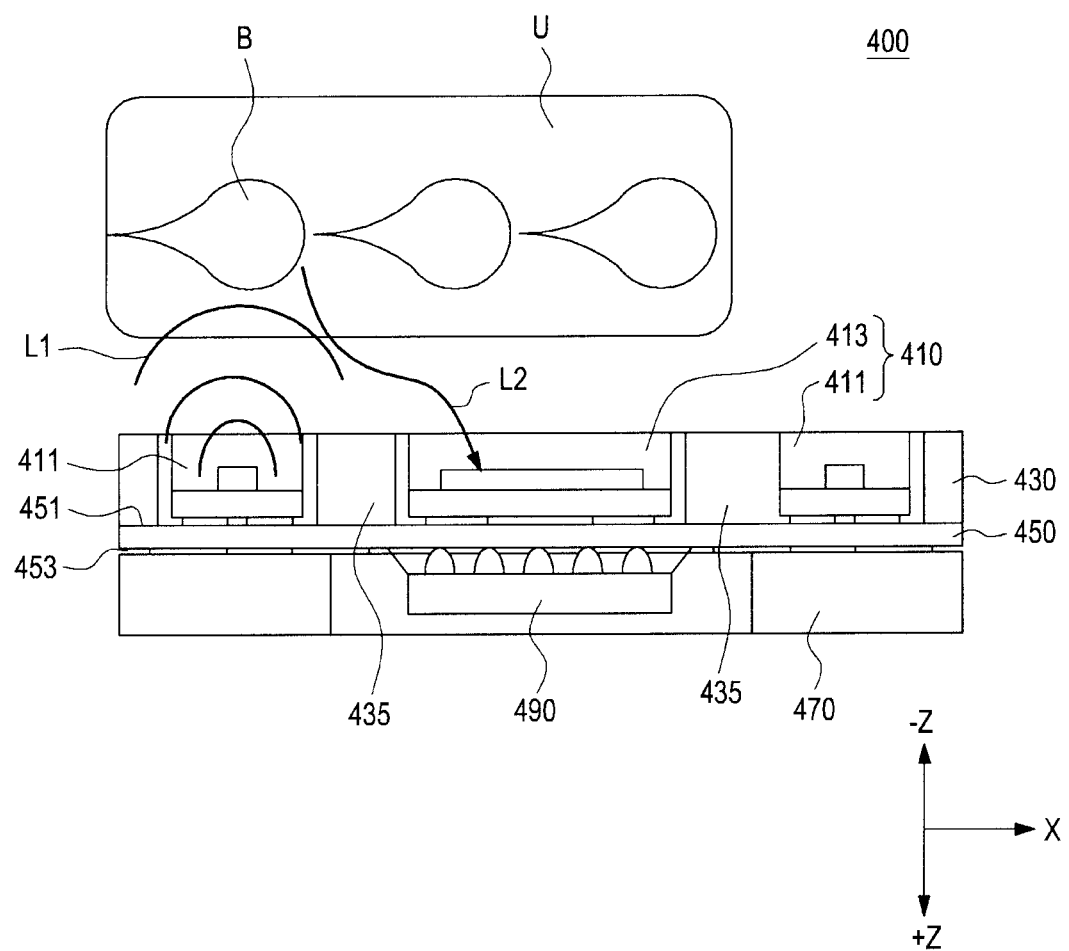
FIG. 7 is a cross-sectional view of the biometric sensor module according to one embodiment of the present disclosure, taken along the line A-A' in FIG. 4.

FIG. 7 is a cross-sectional view of the biometric sensor module according to one embodiment of the present disclosure, taken along the line A-A' in FIG. 4. In FIG. 7, the blood flow in a blood vessel of the user is illustrated.

Figure 8:
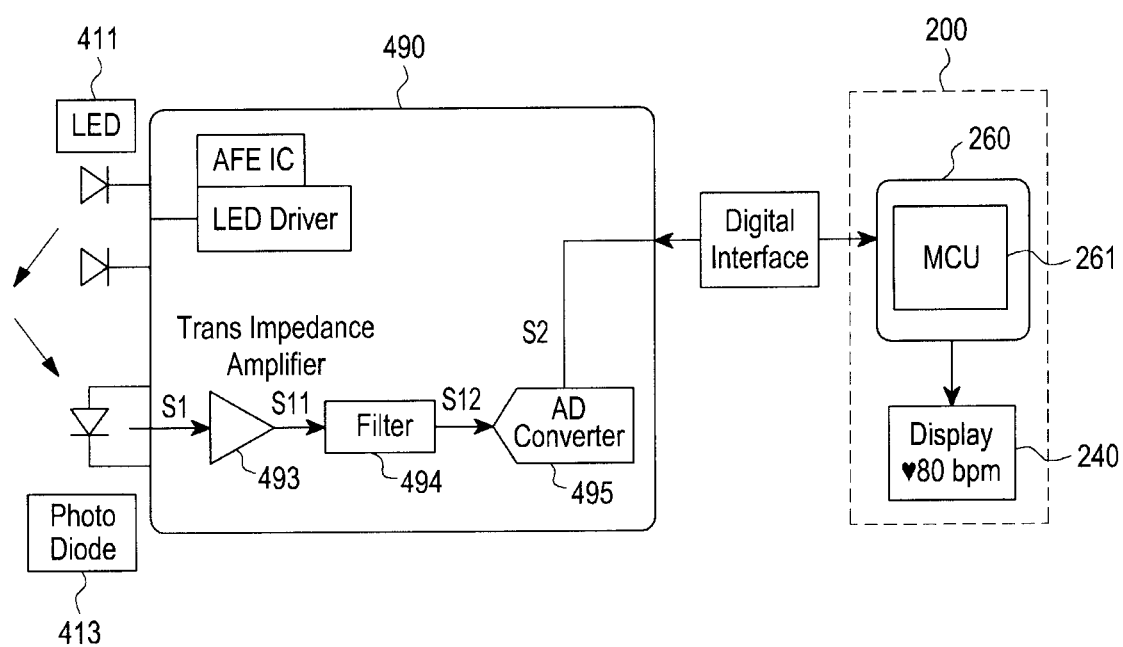
FIG. 8 is a circuit diagram of a biometric sensor module according to one embodiment of the present disclosure.

FIG. 8 is a circuit diagram of a biometric sensor module according to one embodiment of the present disclosure.

Referring to FIGS. 7 and 8, a biometric sensor module 400 according to one embodiment may include a cover unit 430, one or more circuit boards 450 and 470, an optical element unit 410, and an IC element 490. The structure of the cover unit 430, the one or more circuit boards 450 and 470, the optical element unit 410, and the IC element 490 of the biometric sensor module 400 illustrated in FIGS. 7 and 8 may correspond to the structure of the cover unit 330, the one or more circuit boards 350 and 370, the optical element 310, and the IC element 390 of the biometric sensor module 300 illustrated in FIG. 6.

The biometric sensor module 400 may be configured such that the first circuit board 450 and the IC element 490 are sequentially stacked from the optical element unit 410, which is disposed a region in the vicinity of the skin U of the user. The cover unit 430 and the second circuit board 470 may be disposed to surround the optical element unit 410 and the IC unit 490, respectively.

The biometric sensor module 400 may be a smartwatch, and may be used to determine the user's heartbeat using the blood flow B in a blood vessel disposed in the wrist U of the user.

First, the light emitted from the light source 411, which is disposed on the first circuit board 450 exposed to face the second (−Z) direction, may be transmitted to the blood flow B via the first path L1. For example, at least a part of the light emitted from the light source 411 may be absorbed by and/or reflected from the blood flow B in the blood vessel in the user's wrist. The light source 411 may be an LED, and may use green light that can be efficiently transmitted to the blood flow B in the blood vessel in the user's wrist.

The light reflected on the blood flow B may be transmitted to the photodiode 413, which is disposed on the first circuit board 450 exposed to face the second (−Z) direction, via the second path L2 of light. The photodiode 413 may be disposed on the same plane as the light source 411. The photodiode 413 may be configured to be surrounded by a wall 435 disposed between the light source 411 and the photodiode 413 in order to prevent optical interference from the light source 411, for example when light is directly transmitted from the light source 411 to the photodiode 413.

According to one embodiment, when a part of the reflected light is received by the photodiode 413 along the second path L2 of light, the photodiode 413 may convert the reflected light into a first signal. The converted first signal may be transmitted to the IC element 490 disposed on the second face 453 of the first circuit board 450. According to one embodiment, the first signal may be a current signal.

The IC element 490 may convert the first signal S1 received from the photodiode 413 into a second signal S2, and may then transmit the second signal S2 to a control circuit 261 on the main circuit board 260 of the electronic device via a digital interface, such as I2C or an SPI. According to one embodiment, the IC element 490 may include a plurality of processing units, of which the first processing unit 493 may perform operations of converting and amplifying the first signal S1 received from the photodiode 413 into a $(1-a)_{th}$ signal (S11). For example, the first processing unit 493 may be a transimpedance amplifier, and the $(1-a)_{th}$ signal S11 may be a voltage signal.

According to one embodiment, the $(1-a)_{th}$ signal S11 converted by the first processing unit 493 of the IC element 490 may be output as a $(1-b)_{th}$ signal S12 from which noise is removed through the second processing unit 494. For example, the second processing unit 494 may be a Low-Pass Filter (LPF), and may extract the $(1-b)_{th}$ signal S12, from which high frequency noise has been removed by the second processing unit 494.

The $(1-b)_{th}$ signal S12, which has been processed by the second processing unit 494, may be converted by the third processing unit 495, and the converted second signal S2 may be transmitted to the circuit board 260 of the electronic device 200 through a communication method using an I2C protocol, an SPI protocol, or the like. For example, the third processing unit 495 may be an Analog to Digital (AD) converter.

The processing signal transmitted from the third processing unit 495 may be transmitted, as heart rate-related signal which may be easily recognized by the user, to the display device 240 through the preset algorithm executed by the control circuit 261 in the circuit board. The display device 240 may display the heart rate-related signal, thereby providing information to the user. For example, the control circuit 261 may be a Micro Controller Unit (MCU). The display 240 may be disposed to face the first direction so that the user may conveniently check biometric information related to the user's heart rate.

Figure 9:
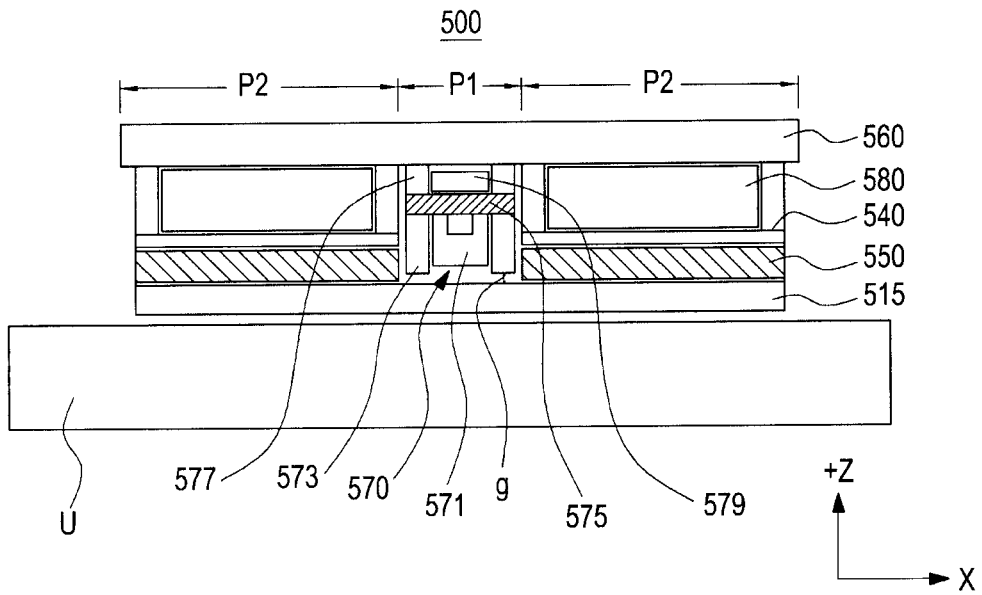
FIG. 9 is a cross-sectional view of the electronic device including the biometric sensor module of FIG. 4, according to one embodiment of the present disclosure, taken along the line B-B' in FIG. 4.

FIG. 9 is a cross-sectional view of the electronic device including the biometric sensor module of FIG. 4, according to one embodiment of the present disclosure, taken along the line B-B' in FIG. 4.

Referring to FIG. 9, a lower portion of an electronic device 500 (e.g. the portion closer to the wrist) worn on the user's wrist is illustrated. The electronic device 500 including a biometric sensor module 570 according to one embodiment of the present disclosure may include a housing, a main circuit board 560, an electronic component 550, and a biometric sensor module 570. The structure of the housing, the main circuit board 560, the electronic component 550, and/or the biometric sensor module 570 of the electronic device 500 illustrated in FIG. 9 may correspond to that of the housing 210, the main circuit board 260, the electronic component 250, and/or the biometric sensor module 270 of the electronic device 200 illustrated in FIGS. 2 to 4.

According to one embodiment, the electronic device 500 including the biometric sensor module 570 may be worn on the user's wrist U in order to sense biometric information in the human body. The biometric sensor module 570 disposed may be disposed such that the optical element 571 faces the wrist U, and may sense biometric information in the human body according to the above-described operation.

The electronic device 500 may include the biometric sensor module 570 disposed below a first region P1 corresponding to the central region of the main circuit board 560. The electronic device 500 may include other electronic components (e.g., a wireless charging antenna) in a region (second region P2) other than the space in which the biometric sensor module 570 is disposed. The electronic component 550, a shielding structure 540, various element circuits 580, and a main circuit board 560 may be sequentially disposed in the second region P2 in the first (+Z) direction from the rear cover 515 of the electronic device 500.

The rear cover 515 of the electronic device 500 may come into contact with the user's wrist, and may be made of glass. On the main circuit board 560, a processor and various component circuits of a communication module and the like may be mounted as an IC chip.

The electronic component 550 may be disposed on the main circuit board 560, and may be a wireless charging antenna. The wireless charging antenna may be a flat coil. The wireless charging antenna may be conductive material in order to generate current by electromagnetic induction from an external electronic device. The current generated in the wireless charging antenna is able to charge the battery disposed inside the electronic device through the main circuit board 560.

According to one embodiment, the biometric sensor module 570 may be disposed below the first region P1 of the main circuit board 560. The biometric sensor module 570 may include a second circuit board 577, a first circuit board 575, and a cover portion 573, which are arranged in the downward (−Z) direction from the main circuit board 560. As another example, an IC element 579 may be disposed inside the second circuit board 577, and an optical element unit 571 may be disposed inside the cover unit 573.

The biometric sensor module 570 may minimize a gap g in order to improve biometric-sensing performance. The adjustment of the thickness of the gap g may be achieved by adjusting the thickness of the second circuit board 577. According to one embodiment, as the gap g is kept as small as possible by adjusting the thickness of the second circuit board 577, the biometric sensor module 570 may be disposed substantially close to the skin of the user (e.g., wrist) so as to improve sensing performance. However, the adjustment of the gap g is not limited to the thickness of the second circuit board 577, and may be implemented through structural design changes in various hardware such as adjusting the thickness of the first circuit board 575 and/or the cover unit 573.

Hereinafter, another embodiment of the biometric sensor module 570 will be described.

Figure 10:
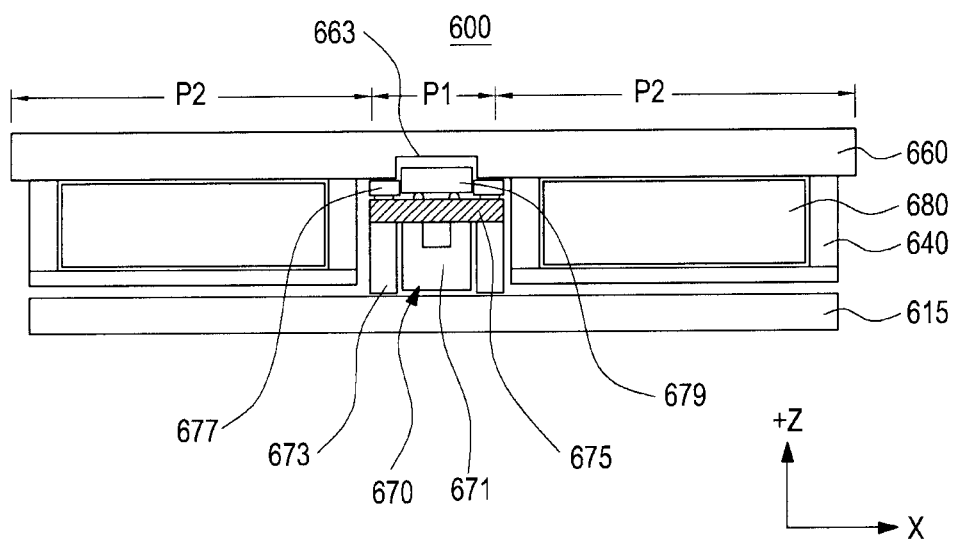
FIG. 10 is a cross-sectional view illustrating the lower end portion of an electronic device including a biometric sensor module, according to one embodiment of the present disclosure.

FIG. 10 is a cross-sectional view illustrating the lower end portion of an electronic device including a biometric sensor module 670, according to one embodiment of the present disclosure.

Referring to FIG. 10, the lower end portion of an electronic device 600 worn on a wearer's wrist is illustrated. The electronic device 600 including a biometric sensor module 670 according to one embodiment of the present disclosure may include a housing, a main circuit board 660, an electronic element 680, and a biometric sensor module 670. The structure of the housing, the main circuit board 660, the electronic element 680, and/or the biometric sensor module 670 of the electronic device 600 illustrated in FIG. 10 may correspond to that of the housing, the main circuit board 560, the electronic component 580, and/or the biometric sensor module 570 of the electronic device 500 illustrated in FIG. 9. Hereinafter, descriptions of the structure of the embodiment of FIG. 9 will be applied to the descriptions of the structure of the embodiment of FIG. 10, and other differences will be described.

According to one embodiment, the biometric sensor module 670 may be disposed below a first region P1 corresponding to a central region of the main circuit board 660. The first region P1 of the main circuit board 660 may include a groove 663 forming a predetermined space in the first (+Z) direction. The groove 663 may be disposed at the center of the first region P1, and may have a size corresponding to a portion of the IC element 679.

The IC element 679 may be disposed in the groove portion 663 of the main circuit board 660 and the second circuit board 677. The thickness of the second circuit board 677 may be smaller compared to the thickness of the second circuit board 577 of FIG. 9. The mounting region occupied by the biometric sensor module 670 may be reduced compared to the structure shown in FIG. 9 due to the IC element 679 seated inside the groove 663.

Figure 11:
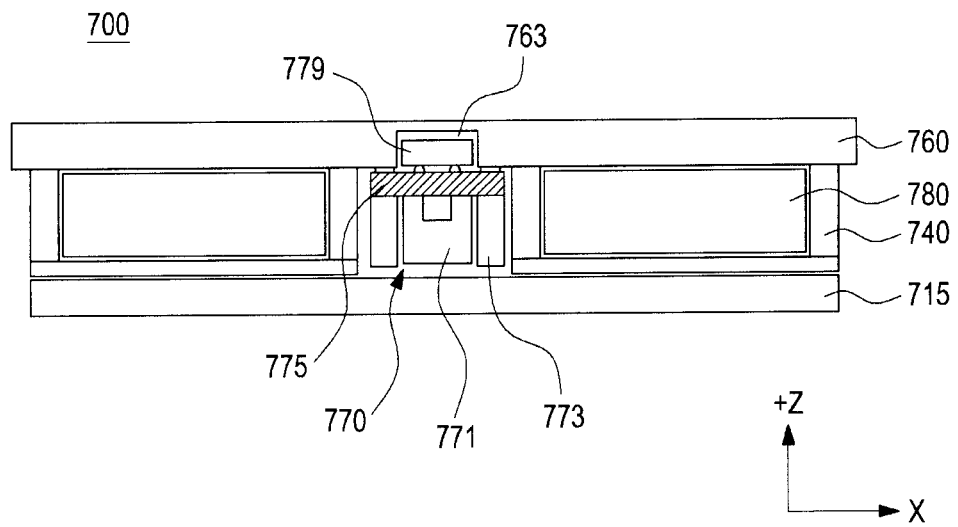
FIG. 11 is a cross-sectional view illustrating the lower end portion of an electronic device including a biometric sensor module, according to one embodiment of the present disclosure.

FIG. 11 is a cross-sectional view illustrating the lower end portion of an electronic device including a biometric sensor module 770, according to one embodiment of the present disclosure.

Referring to FIG. 11, a lower portion of an electronic device 700 worn on a wearer's wrist is illustrated. The electronic device 700 including a biometric sensor module 770 according to one embodiment of the present disclosure may include a housing, a main circuit board 760, an electronic element 780, and a biometric sensor module 770. The structure of the housing, the main circuit board 760, the electronic element 780, and/or the biometric sensor module 770 of the electronic device 700 illustrated in FIG. 11 may correspond to that of the housing, the main circuit board 560, the electronic component 580, and/or the biometric sensor module 570 of the electronic device 500 illustrated in FIG. 9. Hereinafter, descriptions of the structure of the embodiment of FIG. 9 will be applied to the descriptions of the structure of the embodiment of FIG. 11, and other differences will be described.

According to one embodiment, the electronic device 700 worn on the user's wrist may include a shielding structure 740, various element circuits 780, and a main circuit board 760, which may be sequentially disposed in the first (+Z) direction from the rear cover 715.

The biometric sensor module 770 may be disposed below a first region P1 corresponding to a central region of the main circuit board 760. The first region P1 of the main circuit board 760 may include a groove 763 forming a predetermined space in the first (+Z) direction. The groove 763 may be disposed at the center of the first region P1, and may be manufactured to have a size corresponding to the shape of the IC element 779. The IC element 779 may be disposed by being completely inserted into the groove 763.

The IC element 779 may be disposed to be surrounded by the groove portion 763 of the main circuit board 760. According to the embodiment of the present disclosure, the second circuit board 577 of FIG. 9 may be removed. Accordingly, the overall thickness of the electronic device 700 may be reduced.

Figure 12:
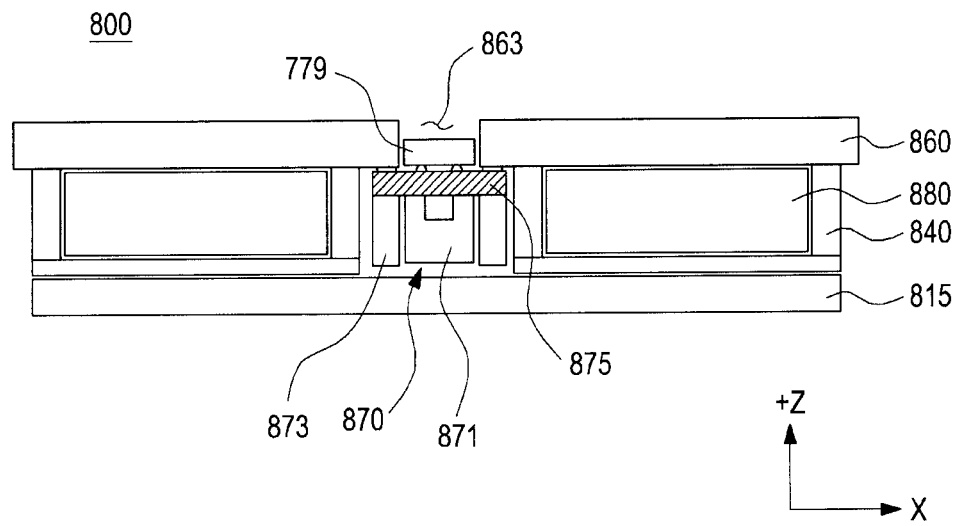
FIG. 12 is a cross-sectional view illustrating the lower end portion of an electronic device including a biometric sensor module, according to one embodiment of the present disclosure.

FIG. 12 is a cross-sectional view illustrating the lower end portion of an electronic device including a biometric sensor module 870, according to one embodiment of the present disclosure.

Referring to FIG. 12, a lower portion of an electronic device 800 worn on a wearer's wrist is illustrated. The electronic device 800 including a biometric sensor module 870 according to one of various embodiments of the present disclosure may include a housing, a main circuit board 860, an electronic element 880, and a biometric sensor module 870. The structure of the housing, the main circuit board 860, the electronic element 880, and/or the biometric sensor module 870 of the electronic device 800 illustrated in FIG. 12 may correspond to that of the housing 510, the main circuit board 560, the electronic component 580, and/or the biometric sensor module 570 of the electronic device 500 illustrated in FIG. 9. Hereinafter, descriptions of the structure of the embodiment of FIG. 9 will be applied to the descriptions of the structure of the embodiment of FIG. 12, and other differences will be described.

According to one embodiment, the electronic device 800 worn on the user's wrist may include a shielding structure 840, various element circuits 880, and a main circuit board 860, which may be sequentially disposed in the first (+Z) direction from the rear cover 815.

The biometric sensor module 870 may be disposed below a first region P1 corresponding to a central region of the main circuit board 860. The first region P1 of the main circuit board 860 may form a hole 863 that penetrates the main circuit board 860. The hole 863 may be disposed at the center of the first region P1, and may be manufactured to have a size corresponding to the shape of the IC element 879. The IC element 879 may disposed by being completely inserted into the hole 863.

The IC element 879 may be disposed to be surrounded by the hole 863 in the main circuit board 860. According to the embodiment of the present disclosure, the second circuit board 577 may be removed. Accordingly, the overall thickness of the electronic device 800 may be reduced.

Figure 13:
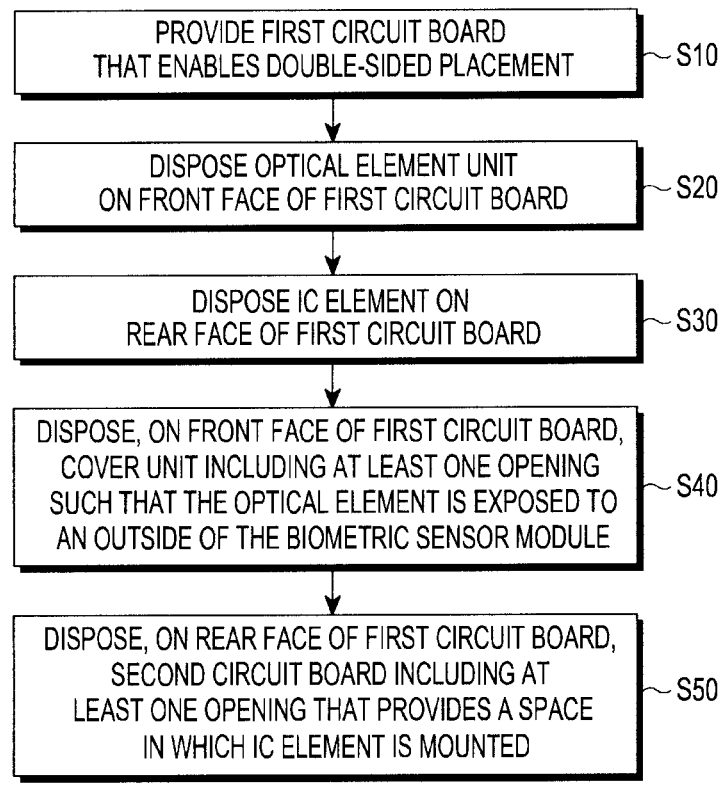
FIG. 13 is a flowchart illustrating an assembly process of the biometric sensor module 300 according to one embodiment of the present disclosure.

FIG. 13 is a flowchart illustrating an assembly process of the biometric sensor module 300 according to one embodiment of the present disclosure. The structure of the cover unit 430, the one or more circuit boards 450 and 470, the optical element unit 410, and the IC element 490 of the biometric sensor module 300 illustrated in FIG. 7 may correspond to the structure of the cover unit 330, the one or more circuit boards 350 and 370, the optical element 310, and the IC element 390 of the biometric sensor module 300 illustrated in FIG. 6.

Referring to FIG. 13, according to Step 10, a first circuit board 350 may be provided, where element circuits may be disposed on opposite faces of the first circuit board 350. Thereafter, the optical element unit 310 may be disposed on the front face of the first circuit board 350 to be electrically connected to the front face according to step 20. The optical element unit 310 may include one or more light sources 311 and a photodiode 313. For example, the one or more light sources 311 may be disposed in an edge region of the first circuit board 350, and may emit light in a direction facing the exterior of the housing. For example, the light source 311 may be an LED module emitting light of various colors. The photodiode 313 may be disposed in the central region of the first circuit board 350. When the light emitted from the light source 311 is reflected by the user's body, the photodiode 313 may receive the reflected light and may convert the received light into current. For example, to measure heartbeat, when a part of the light emitted from the light source 311 is reflected by the blood flow in the blood vessel of the user and received to the photodiode 313, the photodiode 313 may convert the reflected light into a current signal.

After the optical element unit 310 is disposed on the first circuit board 350, the IC element 390 may be disposed on the rear surface of the first circuit board 350 and electrically connected to the rear face of the first circuit board 350 according to step 30. Thus, the first circuit board 350 may be interposed between the optical element unit 310 and the IC element 390. One face of the IC element 390 may be exposed to the exterior of the biometric sensor module 300 so that the IC element 390 may be connected to the main circuit board 260 of the device 200. The IC element 390 may be an analog front-end IC.

The photodiode 313 and the IC element 390 may be arranged on the opposite faces of the first circuit board 350 such that the sizes of each of the elements may differ from one another. For example, if a relatively large photodiode 313 compared with the IC element 390 is arranged on the first circuit board 350, it is possible to ensure a wide light receiving area for the photodiode 313, which may enable the photodiode 313 to detect more accurate biometric signals.

According to the step described above, the IC element 390 is disposed after the optical element unit 310 is disposed on the first circuit board 350. However, without being limited thereto, the optical element unit 310 may be disposed after the IC element 390 is disposed on the first circuit board 350.

After the IC element is disposed, the cover unit 330 including at least one opening may be disposed on the front face of the first circuit board 350 according to step 40. The cover unit 330 may be stacked on the first circuit board 350, and the optical element unit 310 may include one or more openings 331 and 333 and one or more walls 335 that prevents mutual optical signal interference between the photodiode and the light sources. The first opening 331 of the cover unit 330 may be formed in a shape corresponding to the shape of the photodiode 313, and the second openings 333 of the cover unit 330 may be formed in shapes corresponding to the shapes of the light sources 311.

After the cover unit 330 is disposed, the second circuit board 370 may be disposed on the rear face of the first circuit board 350 to provide a mounting space for the IC element 390, according to step 50. The second circuit board 370 may be disposed to face the first circuit board 350. The second circuit board 370 may be manufactured in a plate shape, and may include a third opening 371 that penetrates the upper and lower faces of the second circuit board 370.

According to various embodiments, the IC element 390 may be accommodated inside the space where the third opening 371 is formed, and the IC element 390 disposed inside the third opening 371 may be exposed to face the rear direction. According to various embodiments, the third opening 371 of the second circuit board 370 may be configured to correspond to the shape of the IC element 390.

As described above, according to one embodiment of the present disclosure, an electronic device may include: a housing; an optical element unit that may be configured to emit light toward a user's body, receive light reflected from the user's body, and convert the received light into a first signal; an IC element that may be configured to convert the first signal provided from the optical element unit into a second signal, and provide the second signal to a main circuit board disposed in the housing; a first circuit board that may be disposed between the optical element unit and the IC element and may be electrically connected to the optical element unit and the IC element; and a second circuit board that may include at least one first opening in which the IC element is mounted. The housing may include at least one transparent region such that the light generated by the optical element unit is transmitted through the transparent region to an exterior of the housing.

According to one embodiment, the first signal may include a measurement of a change in a flow rate of blood flowing in a blood vessel of the user.

According to one embodiment, the first circuit board may include a first face facing the optical element unit and a second face facing the IC element, and the first face may be electrically connected to the optical element unit and the second face may be electrically connected to the IC element.

According to one embodiment, the optical element unit may include: at least one light source that may be configured to emit the light toward the user's body; and a photodiode that may be configured to receive the light reflected from the user's body and convert the received light into the first signal.

According to one embodiment, the emitted light may have a wavelength in a range of about 450 nm to 600 nm.

According to one embodiment, the electronic device may include a cover unit. The cover unit may include: at least one second opening in which the at least one light source is mounted, such that the at least one light source is exposed toward the user's body; and at least one third opening in which the photodiode is mounted, such that the photodiode is exposed toward the user's body.

According to one embodiment, the light emitted from the at least one light source may be reflected by a blood flow of the user and may be received by the photodiode, and the cover unit may include a wall disposed between the second opening and the third opening to prevent optical interference between the at least one light source and the photodiode.

According to one embodiment, when viewed from a direction orthogonal to the at least one transparent region, the photodiode may at least partially overlap the IC element.

According to one embodiment, the photodiode and the IC element may be disposed to be opposite each other with the first circuit board being interposed therebetween, and an area of the photodiode may be larger than an area of the IC element.

According to one embodiment, an entire area of the second circuit board may be disposed to substantially overlap an entire area of the first circuit board.

According to one embodiment, the second circuit board may be disposed between the first circuit board and the main circuit board, and may provide electrical connection between the first circuit board and the main circuit board.

According to one embodiment, the first opening may be disposed in a central region of the second circuit board, and the first opening may have a thickness that is larger than a thickness of the IC element.

According to one embodiment, the IC element may include a plurality of processing units, which may include: a first processing unit that may be configured to convert and amplify the first signal into a $(1-a)_{th}$ signal; a second processing unit that may be configured to remove noise of the $(1-a)_{th}$ signal to generate a $(1-b)_{th}$ signal; and a third processing unit that may be configured to generate the second signal by converting the $(1-b)_{th}$ signal into a digital signal.

According to one embodiment, the main circuit board may include a control circuit that may output the second signal transmitted from the IC element as the user's heart rate signal by executing a predetermined algorithm, and may display the signal on a display device.

According to one embodiment, the photodiode and the IC element may be disposed in a central portion of the first circuit board, and the at least one light source may include a plurality of light sources that may be disposed in an edge region of the first circuit board with the photodiode interposed therebetween.

According to one embodiment, the main circuit board may be disposed between a display device and the first circuit board and may include a concave groove, such that at least a portion of the IC element is mounted inside the groove, and the second circuit board is disposed to face an edge of the groove.

According to one embodiment, the electronic device may include: a housing; a biometric sensor module that may be disposed in the housing and may be configured to detect biometric information of a user; and a main circuit board that may be disposed adjacent to the biometric sensor module and may include at least one hole or groove.

According to one embodiment, the biometric sensor module may include: an optical element unit; an IC element inserted into the at least one hole or groove of the main circuit board, the IC element may be configured to convert a signal provided from the optical element unit and provide the converted signal to the main circuit board; a first circuit board that may include a first face on which the optical element unit is disposed and a second face which is opposite the first face and on which the IC element is disposed; and a cover unit that may include at least one opening, such that the optical element unit is exposed toward the user's body.

According to one embodiment, there is provided a biometric sensor module disposed in an electronic device. The biometric sensor module may include: a first circuit board; an optical element unit that may be disposed on a front face of the first circuit board; an IC element that may be disposed on a rear face of the first circuit board; a cover unit that may be disposed on the front face of the first circuit board and may include at least one first opening such that the optical element unit is exposed toward a user's body; and a second circuit board that may be disposed on the rear face of the first circuit board and may include at least one second opening in which the IC element is mounted.

According to one embodiment, the at least one second opening of the second circuit board may be disposed in a central region of the second circuit board, and an area of a photodiode of the optical element unit may be larger than an area of the IC element.

According to one embodiment, there is provided a method of assembling a biometric sensor module disposed in an electronic device. The method may include: providing a first circuit board configured to mount electronic components on both sides of the first circuit board; disposing an optical element unit on a front face of the first circuit board; disposing an IC element on a rear face of the first circuit board; disposing, on the front face of the first circuit board, a cover unit including at least one first opening such that the optical element is exposed toward a user's body; and disposing, on the rear face of the first circuit board, a second circuit board including at least one second opening in which the IC element is mounted.

Aspects of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the present disclosure has been shown and described with reference to certain embodiments thereof, it will be apparent to those skilled in the art that the biometric sensor module according to the present disclosure is not limited to these embodiments, and various changes in form and details may be made therein without departing from the spirit and scope of the present disclosure as defined by the appended claims.

What is claimed is:

1. An electronic device comprising:
   a housing;
   an optical element unit configured to emit light toward a user's body, receive light reflected from the user's body, and convert the received light into a first signal;
   an IC element configured to convert the first signal provided from the optical element unit into a second signal, and provide the second signal to a main circuit board disposed in the housing;
   a first circuit board disposed between the optical element unit and the IC element and is electrically connected to the optical element unit and the IC element; and
   a second circuit board including at least one first opening in which the IC element is mounted,
   wherein the housing includes at least one transparent region such that the light generated by the optical element unit is transmitted through the transparent region to an exterior of the housing,
   wherein the main circuit board is disposed between a display device and the first circuit board and includes a hole or groove disposed to correspond to the at least one first opening, and wherein a first thickness of the IC element is greater than a second thickness of the second circuit board, such that a first portion of the IC element is accommodated in the at least one first opening and a remaining portion of the IC element is accommodated in the hole or groove.

2. The electronic device of claim 1, wherein the first signal includes a measurement of a change in a flow rate of blood flowing in a blood vessel of the user.

3. The electronic device of claim 1, wherein the first circuit board includes a first face facing the optical element unit and a second face facing the IC element, and wherein the first face is electrically connected to the optical element unit and the second face is electrically connected to the IC element.

4. The electronic device of claim 1, wherein the optical element unit includes:
at least one light source configured to emit the light toward the user's body; and
a photodiode configured to receive the light reflected from the user's body and convert the received light into the first signal.

5. The electronic device of claim 1, wherein the emitted light has a wavelength in a range of about 450 nm to 600 nm.

6. The electronic device of claim 4, further comprising: a cover unit including:
at least one second opening in which the at least one light source is mounted, such that the at least one light source is exposed toward the user's body; and
at least one third opening in which the photodiode is mounted, such that the photodiode is exposed toward the user's body.

7. The electronic device of claim 6, wherein the light emitted from the at least one light source is reflected by a blood flow of the user and is received by the photodiode, and the cover unit includes a wall disposed between the second opening and the third opening to prevent optical interference between the at least one light source and the photodiode.

8. The electronic device of claim 4, wherein the at least one transparent region defines a plane, and wherein, when viewed from a direction orthogonal to the plane of the at least one transparent region, the photodiode at least partially overlaps the IC element.

9. The electronic device of claim 4, wherein the photodiode and the IC element are disposed to be opposite each other with the first circuit board being interposed therebetween, and an area of the photodiode is larger than an area of the IC element.

10. The electronic device of claim 1, wherein an entire area of the second circuit board is disposed to substantially overlap an entire area of the first circuit board.

11. The electronic device of claim 10, wherein the second circuit board is disposed between the first circuit board and the main circuit board, and provides electrical connection between the first circuit board and the main circuit board.

12. The electronic device of claim 11, wherein the at least one first opening is disposed in a central region of the second circuit board.

13. The electronic device of claim 1, wherein the IC element includes a plurality of processing units including:
a first processing unit configured to convert and amplify the first signal into a (1-a)th signal;
a second processing unit configured to remove noise of the (1-a)th signal to generate a (1-b)th signal; and
a third processing unit configured to generate the second signal by converting the (1-b)th signal into a digital signal.

14. The electronic device of claim 1, wherein the main circuit board includes a control circuit configured to:
output the second signal transmitted from the IC element as the user's heart rate signal by executing a predetermined algorithm, and
display the user's heart rate signal on a display device.

15. The electronic device of claim 4, wherein the photodiode and the IC element are disposed in a central portion of the first circuit board, and the at least one light source includes a plurality of light sources that are disposed in an edge region of the first circuit board with the photodiode interposed therebetween.

16. An electronic device comprising:
a housing;
a biometric sensor module disposed in the housing and configured to detect biometric information of a user; and
a main circuit board disposed adjacent to the biometric sensor module and including at least one hole or groove,
wherein the biometric sensor module includes:
an optical element unit;
an IC element configured to convert a signal provided from the optical element unit and provide the converted signal to the main circuit board;
a first circuit board including a first face on which the optical element unit is disposed and a second face which is opposite the first face and on which the IC element is disposed;
a second circuit board including at least one first opening in which the IC element is mounted; and
a cover unit including at least one second opening, such that the optical element unit is exposed toward the user's body,
wherein a first thickness of the IC element is greater than a second thickness of the second circuit board, such that a first portion of the IC element is accommodated in the at least one first opening and a remaining portion of the IC element is accommodated in the hole or groove of the main circuit board.

17. A biometric sensor module comprising:
a first circuit board;
an optical element unit disposed on a front face of the first circuit board;
an IC element disposed on a rear face of the first circuit board;
a cover unit disposed on the front face of the first circuit board and including at least one first opening such that the optical element unit is exposed toward a user's body; and
a second circuit board disposed on the rear face of the first circuit board and including at least one second opening in which the IC element is mounted.

18. The biometric sensor module of claim 17, wherein the at least one second opening of the second circuit board is disposed in a central region of the second circuit board, and wherein an area of a photodiode of the optical element unit is larger than an area of the IC element.

* * * * *